United States Patent
Hibner et al.

(10) Patent No.: US 11,191,601 B2
(45) Date of Patent: Dec. 7, 2021

(54) DISTALLY REPLACEABLE CABLE SYSTEMS IN SURGICAL TOOLS

(71) Applicant: Ethicon LLC, Guaynabo, PR (US)

(72) Inventors: John Hibner, Mason, OH (US); Thomas Remm, Milford, OH (US)

(73) Assignee: Cilag GmbH International, Zug (CH)

( * ) Notice: Subject to any disclaimer, the term of this patent is extended or adjusted under 35 U.S.C. 154(b) by 64 days.

(21) Appl. No.: 16/854,047

(22) Filed: Apr. 21, 2020

(65) Prior Publication Data

US 2020/0246097 A1   Aug. 6, 2020

Related U.S. Application Data

(62) Division of application No. 15/790,385, filed on Oct. 23, 2017, now Pat. No. 10,639,116.

(51) Int. Cl.
| | | |
|---|---|---|
| *A61B 34/00* | (2016.01) | |
| *A61B 34/30* | (2016.01) | |
| *A61B 17/00* | (2006.01) | |
| *A61B 17/34* | (2006.01) | |

(52) U.S. Cl.
CPC ........ *A61B 34/71* (2016.02); *A61B 17/00234* (2013.01); *A61B 17/34* (2013.01); *A61B 34/30* (2016.02); *A61B 2017/0023* (2013.01); *A61B 2017/00477* (2013.01)

(58) Field of Classification Search
CPC ... A61B 34/71; A61B 2034/715; A61B 17/00; B21F 15/06; B21F 45/008; F16G 11/08
See application file for complete search history.

(56) References Cited

U.S. PATENT DOCUMENTS

| | | | | |
|---|---|---|---|---|
| 4,252,992 | A * | 2/1981 | Cherry ..................... | H01R 4/08 174/84 R |
| 5,797,900 | A * | 8/1998 | Madhani .................... | B25J 3/04 606/1 |
| 6,786,896 | B1 * | 9/2004 | Madhani ................ | B25J 9/1615 606/1 |
| 8,831,782 | B2 | 9/2014 | Itkowitz | |
| 8,961,061 | B2 * | 2/2015 | Wahlberg .............. | F16G 11/025 403/275 |

(Continued)

FOREIGN PATENT DOCUMENTS

| | | |
|---|---|---|
| WO | 2014151621 A1 | 9/2014 |
| WO | 2014151952 A1 | 9/2014 |

*Primary Examiner* — Christopher M Koehler
(74) *Attorney, Agent, or Firm* — Vorys, Sater, Seymour and Please LLP

(57) ABSTRACT

A method of replacing cables in a cable-driven surgical tool includes accessing a cable system of the cable-driven surgical tool, the cable-driven surgical tool including a shaft and an end effector operatively coupled to the distal end of the shaft. The cable system comprises distal and proximal cable portions extending within the shaft and adjoined by a releasable interconnect, the distal cable portion being operatively coupled to the end effector. The distal and proximal cable portions are disconnectable at the releasable interconnect, wherein the distal cable portion exhibits a first diameter and the proximal cable portion exhibits a second diameter greater than the distal cable portion. The distal cable portion is then removed and replaced with a replacement distal cable portion mated to the proximal cable portion.

20 Claims, 12 Drawing Sheets

(56) References Cited

U.S. PATENT DOCUMENTS

| | | |
|---|---|---|
| 2006/0052664 A1 | 3/2006 | Julian |
| 2011/0184241 A1* | 7/2011 | Zubiate .................. A61B 34/30 |
| | | 600/141 |
| 2012/0123200 A1* | 5/2012 | Rogers ............. A61B 17/00234 |
| | | 600/104 |
| 2015/0313676 A1 | 11/2015 | Deodhar |
| 2016/0287252 A1 | 10/2016 | Parihar |
| 2019/0111236 A1* | 4/2019 | Oliverius .......... A61M 25/0147 |

* cited by examiner

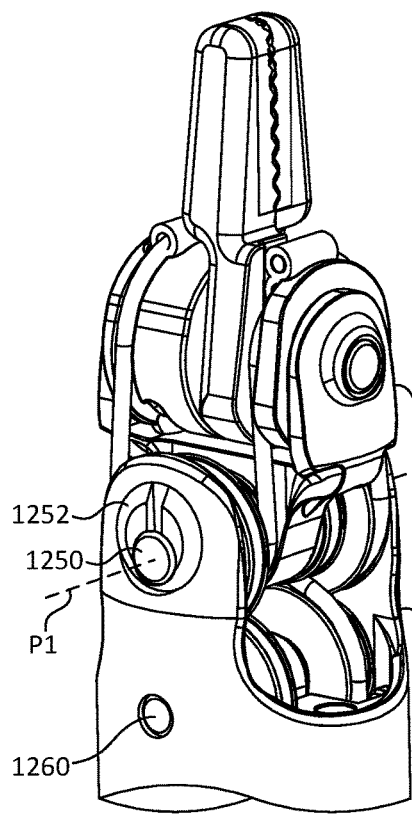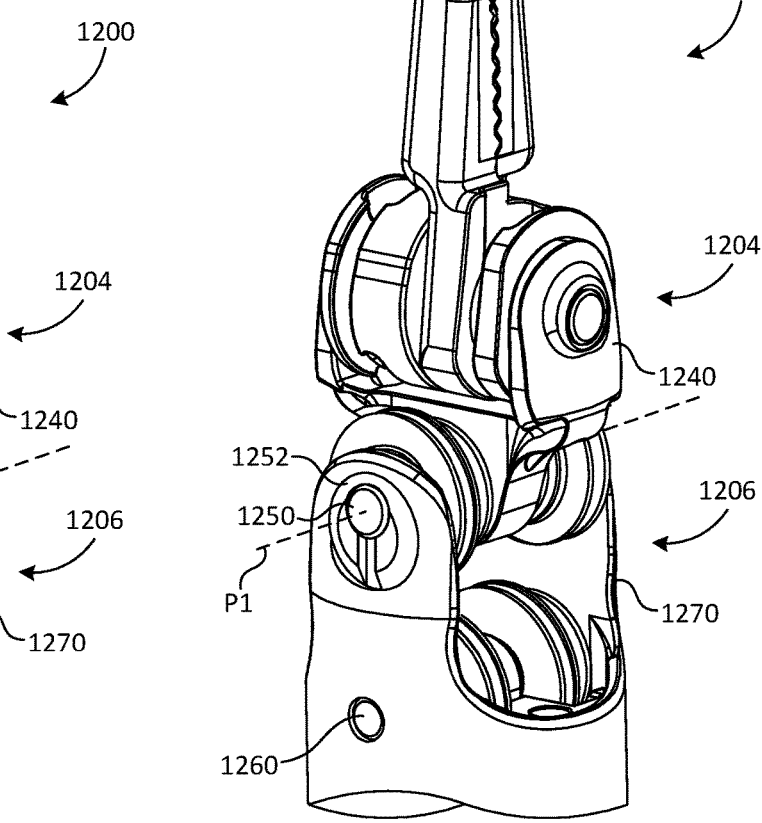
FIG. 12A   FIG. 12B
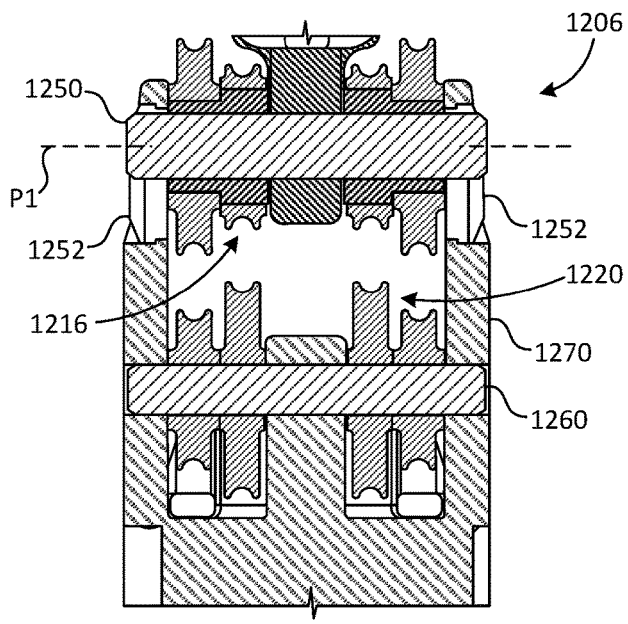
FIG. 12C

DISTALLY REPLACEABLE CABLE SYSTEMS IN SURGICAL TOOLS

BACKGROUND

Minimally invasive surgical (MIS) tools and procedures can often be preferred over traditional open surgical techniques due to their ability to decrease post-operative recovery time and to leave minimal scarring. Laparoscopic surgery is one type of MIS procedure in which one or more small incisions are formed in the abdomen of a patient and a trocar is inserted through each incision to provide a surgical access pathway for an appropriate surgical tool. Trocars can additionally provide an internal seal assembly for maintaining insufflation of the abdomen during a surgical procedure.

A variety of MIS tools can be inserted into the abdominal cavity of a patient via a trocar and maneuvered from outside the abdomen. Laparoscopic surgical tools, for example, are often similar to those used in traditional surgical procedures, with the exception that laparoscopic surgical tools possess an elongate shaft extending from an end effector to a location outside the abdomen. The end effector is the surgically functional part of the surgical tool. The shaft protrudes externally through a trocar when the surgical tool is inserted in the abdomen of a patient, and an external portion of the surgical tool provides a means for manipulating and communicating with the end effector. Once inserted in a patient's body, the end effector can engage and/or treat tissue in a number of ways to achieve a desired diagnostic or therapeutic effect. Illustrative end effectors of laparoscopic and similar surgical tools include, but are not limited to, scissors, graspers, needle drivers, clamps, staplers, cauterizers, suction tools, irrigation tools, clip-appliers, and the like.

Robotic surgery represents a specialized class of laparoscopic surgical procedures. Instead of directly engaging a surgical tool, as in traditional laparoscopic surgery, a surgeon instead manipulates and engages the surgical tool using an electronic interface communicatively coupled to a robotic manipulator. Manipulation and engagement of a surgical tool under robotic control can allow much more precise surgical procedures to be performed in many instances. A surgeon need not necessarily even be in the operating room with the patient. Advantageously, robotic surgical systems can allow intuitive hand movements to be realized by maintaining a natural eye-hand axis. In addition, robotic surgical systems can incorporate a "wrist" at the end effector to provide natural, hand-like articulation during a robotic surgical procedure. The wrist can also facilitate an expanded and more complex range of motion than is possible with a human wrist, which can allow highly elaborate and precise surgical procedures to be performed.

In robotic surgery, one or more arms of a robotic manipulator are mounted to corresponding surgical tools, and the tool(s) is/are manipulated and engaged under the direction of a surgeon during a surgical procedure. Each arm has one or more joints to facilitate manipulation of its attached surgical tool and a mounting fixture to promote the tool's attachment with a complementary housing at the proximal end of the tool. The housing includes one or more mechanisms for actuating the end effector, such as a system for instigating movement of the end effector upon a suitable input from the mounting fixture. For example, the mounting fixture may include one or more drive couplers (e.g., rotary or linear drive couplers) configured to engage a suitable component in the housing and produce a corresponding motion in the end effector (e.g., rotation, pitch, yaw or actuation).

Most conventional laparoscopic surgical tools, including robotic surgical tools, employ multiple elongate members that pass through the elongate shaft within a lumen and establish mechanical communication between the mechanism in the housing and the end effector. Specifically, in many instances, the elongate members deploy or retract in response to a mechanical input from the mounting fixture and housing to convey surgical instructions to the end effector. Illustrative elongate members within laparoscopic and similar surgical tools include, for example, high-durability cables, bands, lines, cords, wires, ropes, strings, twisted strings or like structures that extend continuously from the housing to the end effector. These and similar elongate members are collectively referred to herein as "cables". Similarly, surgical tools containing such cables may be referred to herein as "cable-driven surgical tools."

One drawback of laparoscopic and similar cable-driven surgical tools is that their cables are prone to weakening (fatigue) and wear over time, especially where the cables interact with the end effector and are forced into curved shapes (e.g., where contacting internal pulleys). Cable weakening can lead to slackening, which may lessen the end effector's movement precision and possibly compromise the safety and effectiveness of a surgical procedure. Further cable slackening can lead to derailment from the mechanism within the housing or elsewhere. Extreme cable weakening can even lead to catastrophic cable failure (breakage) in some instances. As a result, laparoscopic and similar cable-driven surgical tools are commonly taken out of service well in advance of the time at which cable weakening and wear are anticipated to become problematic.

Once a conventional laparoscopic or similar cable-driven surgical tool is taken out of service due to cable weakening and wear, there is usually no way to recondition the tool effectively without disassembling it nearly completely. In many cases, conventional laparoscopic and similar cable-driven surgical tools may be discarded once taken out of service due to the difficulty of disassembly and refurbishment, despite many of the other tool components remaining within their usable lifetimes.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 12A-C show diagrams illustrating one approach for generating clearance in a wrist of a cable-driven surgical tool.

DETAILED DESCRIPTION

The present disclosure generally describes cable-driven surgical tools and, more specifically, cable-driven surgical tools in which the distal end of one or more cables can be readily replaced.

As discussed above, cable weakening and wear commonly occur in cable-driven surgical tools. Worn or broken cables can be very difficult to replace in conventional cable-driven surgical tools. At present, discarding a cable-driven surgical tool with worn or broken cables may be preferable to attempting its refurbishment. Advantageously, the present disclosure provides cable-driven surgical tools and methods in which the cables and similar elongate members can be readily replaced. More specific advantages are discussed hereinbelow.

Before discussing how the present disclosure addresses the issue of cable replacement in cable-driven surgical tools, a brief overview of conventional cable-driven surgical tools will be provided hereinafter in order for the embodiments of the present disclosure to be better understood. Many of the concepts and features discussed hereinafter are also applicable to the cable-driven surgical tools and methods of the present disclosure. The cable-driven surgical tools of the present disclosure may be configured as robotic surgical tools (i.e., by being compatible with the mounting fixture of a robotic manipulator), although they may be configured as conventional laparoscopic surgical tools in alternative embodiments (i.e., by being capable of direct engagement by a surgeon).

The terms "proximal" and "distal" are defined herein relative to the location of engagement by a surgeon or a robotic manipulator. The term "proximal" refers to a position closer to the location of engagement, and the term "distal" refers to a position more removed from the location of engagement. Moreover, directional terms such as above, below, upper, lower, upward, downward, left, right, and the like are used to describe relative position in the figures and thus should not be considered limiting.

Figure 1:
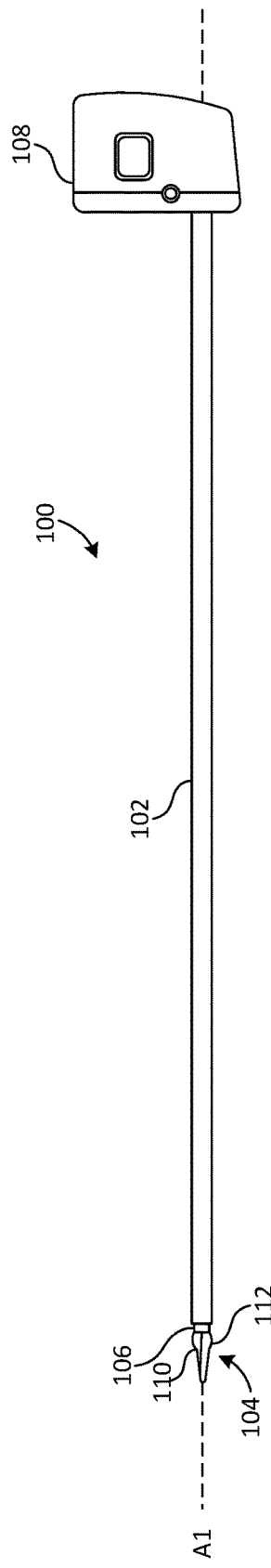
FIG. 1 shows a diagram of an illustrative cable-driven surgical tool that may incorporate certain principles of the present disclosure.

FIG. 1 shows a diagram of an illustrative cable-driven surgical tool 100 that may incorporate certain principles of the present disclosure. Cable-driven surgical tool 100 includes elongate shaft 102, end effector 104 located at a distal end of elongate shaft 102, and housing 108 located at a proximal end of elongate shaft 102. Wrist 106 is also located at a distal end of elongate shaft 102 and couples end effector 104 thereto. Housing 108 of cable-driven surgical tool 100 may be configured for releasable coupling with a mounting fixture of a robotic manipulator (not shown in FIG. 1), alternately referred to as a "robot" or "surgical robot." In some alternative embodiments, housing 108 may be configured for actuating end effector 104 upon engagement by a surgeon or a robotic manipulator. User inputs to housing 108 therefore control operation of end effector 104 via the cables or similar elongate members (obscured in FIG. 1).

In one or more embodiments, housing 108 may be configured for releasable coupling with a mounting fixture of a robotic manipulator. Housing 108 may be releasably coupled with the mounting fixture in a variety of ways, such as by clamping or clipping thereto, or slidably mating therewith. Illustrative mechanisms for coupling housing 108 to a mounting fixture are described in more detail in U.S. Patent Application Publications 2015/0209965 and 2015/0025549, incorporated herein by reference in their entirety, and U.S. patent application Ser. No. 15/200,283, filed on Jul. 1, 2016 and entitled "Methods, Systems, And Devices For Initializing A Surgical Tool," which is also incorporated herein by reference in its entirety. Illustrative robotic surgical systems are also described in these references as well as in U.S. Pat. No. 8,831,782, which is also incorporated herein by reference in its entirety.

Continuing with FIG. 1, end effector 104 is configured to move relative to elongate shaft 102 at wrist 106, such as by pivoting at wrist 106, to position end effector 104 at a desired orientation and location relative to a surgical site during a surgical procedure. Housing 108 includes various components designed to position and operate various features of end effector 104 (e.g., one or more of clamping, firing, rotation, articulation, energy delivery, and the like). In illustrative embodiments, one or more cables (obscured in FIG. 1) can extend from housing 108 through wrist 106 to facilitate movement of end effector 104, as discussed in more detail herein. In at least some embodiments, elongate shaft 102 and end effector 104 coupled distally thereto are configured to rotate about longitudinal axis A1. In some embodiments, various components of housing 108 can be configured to facilitate rotational motion of elongate shaft 102 and end effector 104 about longitudinal axis A1. In other embodiments, elongate shaft 102 may be fixed to housing 108, in which case cable-driven surgical tool 100 may be rotated by the robotic manipulator to reposition elongate shaft 102 and end effector 104.

Cable-driven surgical tool 100, particularly at end effector 104, can be configured to perform at least one surgical function. The choice of end effector 104 can determine which surgical function cable-driven surgical tool 100 is able to perform. Illustrative configurations of end effector 104 that may be present in cable-driven surgical tool 100 include, for example, forceps, graspers, needle drivers, scissors, electrocauterization tools that apply energy to tissue, staplers, clip appliers, suctioning tools, irrigation tools, imaging devices (e.g., endoscopes or ultrasonic probes), and any combination thereof. In at least one embodiment, cable-driven surgical tool 100 may be configured to apply mechanical force to a tissue. The mechanical force can be conveyed via the cables or similar elongate members in mechanical communication with end effector 104.

Elongate shaft 102 extends distally from housing 108 and has at least one lumen (see FIG. 3) extending internally therethrough. Elongate shaft 102 may be affixed to housing 108, but alternately may be releasably coupled so as to be interchangeable with other types of shafts, such as shafts have a differing diameter. In at least some embodiments, elongate shaft 102 may be rotatably coupled to housing 108.

End effector 104 can have a variety of sizes, shapes and configurations. In the illustrative configuration of FIG. 1, end effector 104 comprises a tissue grasper or needle driver having opposing jaws 110 and 112 that are configured to move (pivot) between open and closed positions. In addition, the entirety of end effector 104 may pivot relative to elongate shaft 102 at wrist 106. Pivoting may place end effector 104 in a better position to engage tissue during a surgical procedure. The pivoting of end effector 104 may be cable-driven. Other suitable cable-driven configurations for end effector 104 include, but are not limited to, scissors including a pair of opposed cutting jaws, babcocks including a pair of opposed grasping jaws, retractors, and the like. Additional configurations for end effector 104 are also provided above.

Wrist 106 can likewise have a variety of configurations. In the illustrative configuration of FIG. 1, wrist 106 includes a joint configured to allow movement of end effector 104 relative to elongate shaft 102, such as a pivot joint at which jaws 110 and 112 are pivotally attached. Illustrative configurations that may be similar to wrist 106 that are suitable for use in the embodiments of the present disclosure include those described in U.S. Patent Application Publications 2015/0209965 and 2015/0025549 and U.S. patent application Ser. No. 15/200,283, each previously incorporated by reference above. Additional discussion of the configuration of wrist 106 and similar wrists is provided hereinbelow in regard to the illustrative embodiments of the present disclosure.

Figure 2:
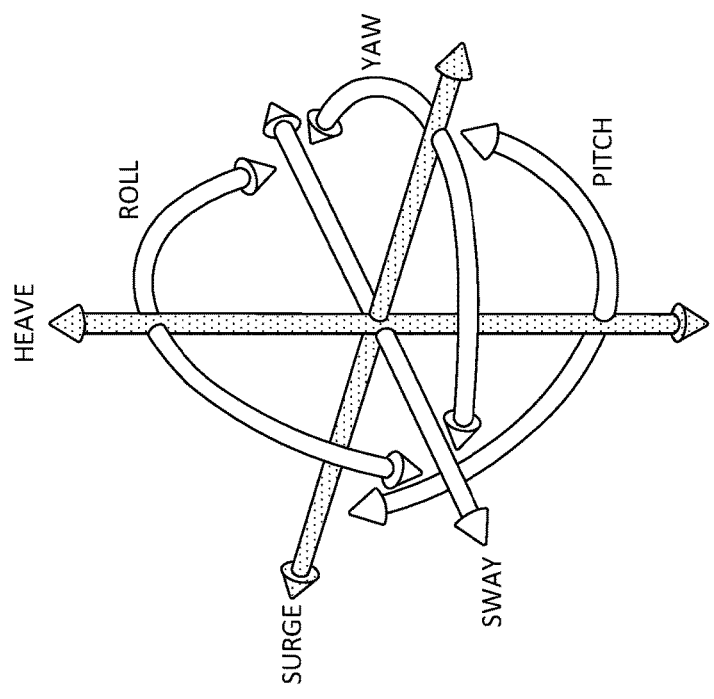
FIG. 2 shows a diagram illustrating the degrees of freedom through which a wrist of a surgical tool may articulate.

FIG. 2 shows a diagram illustrating the degrees of freedom through which wrist 106 may articulate. More specifically, the degrees of freedom available to wrist 106 are represented by three translational or position variables (e.g., surge, heave and sway) and three rotational or orientation variables (e.g., Euler angles or roll, pitch and yaw). The translational and rotational variables collectively describe the position and orientation of one or more components of a surgical system (e.g., wrist 106 and associated end effector 104) with respect to a given frame of reference, such as a Cartesian coordinate system or spherical coordinate system. As illustrated in FIG. 2, the term "surge" refers to forward and backward movement, the term "heave" refers to up and down movement, and the term "sway" refers to left and right movement. With regard to the rotational terms in FIG. 2, "roll" refers to side-to-side tilting, "pitch" refers to forward and backward tilting, and "yaw" refers to left and right turning.

In some embodiments, a pivoting motion can include pitch movement about a first axis of wrist 106 (e.g., X-axis), yaw movement about a second axis of wrist 106 (e.g., Y-axis), and combinations thereof to allow for 360° rotational movement of end effector 104 about wrist 106. In other embodiments, a pivoting motion can be limited to movement in a single plane such that end effector 104 rotates only in a single plane (e.g., only pitch movement about a first axis of wrist 106 or only yaw movement about a second axis of wrist 106).

Cable-driven surgical tool 100 includes a plurality of elongate members (obscured in FIG. 1 and synonymously referred to herein as "cables"), which are configured to impart movement to end effector 104 relative to elongate shaft 102. Illustrative forms of the elongate members include, for example, cables, bands, lines, cords, wires, ropes, strings, twisted strings and the like. Cables and similar elongate members can be formed from any of a variety of high-durability materials, such as a metal (e.g., tungsten, stainless steel, and like materials) or a polymer. In at least one embodiment, one or more of the elongate members may be made of a flexible material. Illustrative cables and similar elongate members are described in U.S. Patent Application Publications 2015/0209965 and 2015/0025549, previously incorporated herein by reference.

Figure 3:
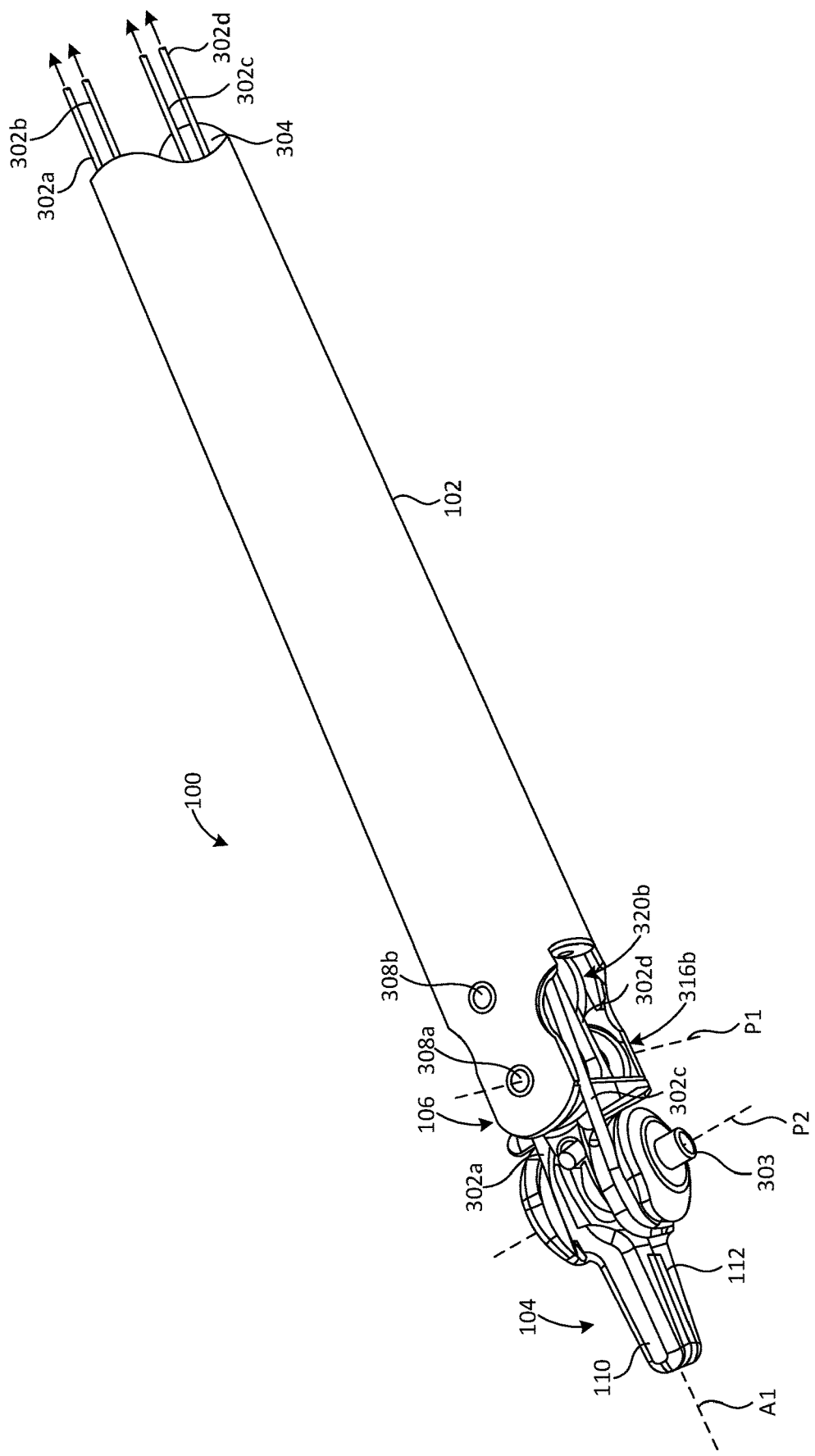
FIGS. 3-5 show various views of an illustrative cable-driven surgical tool.
Figure 4:
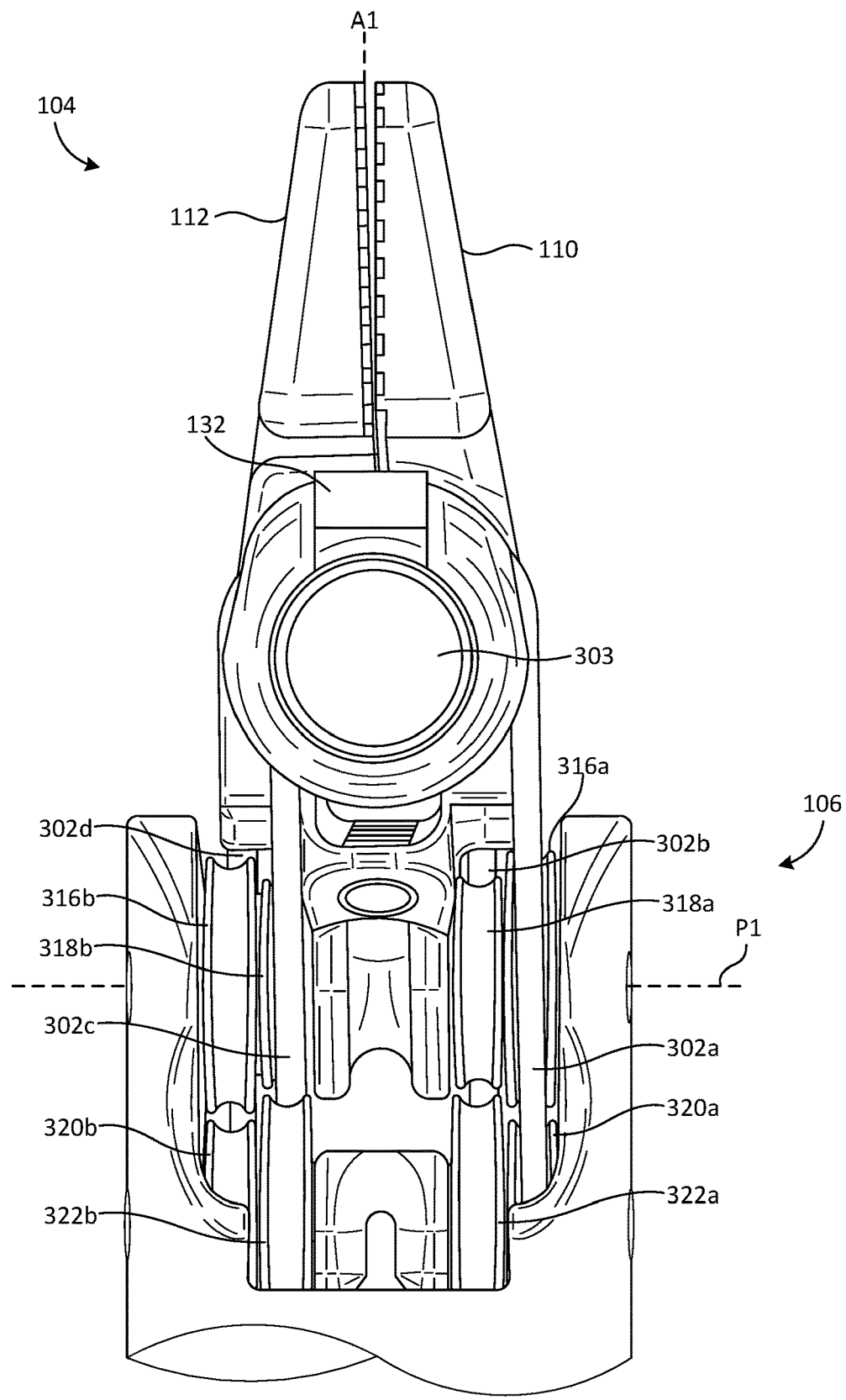
Figure 5:
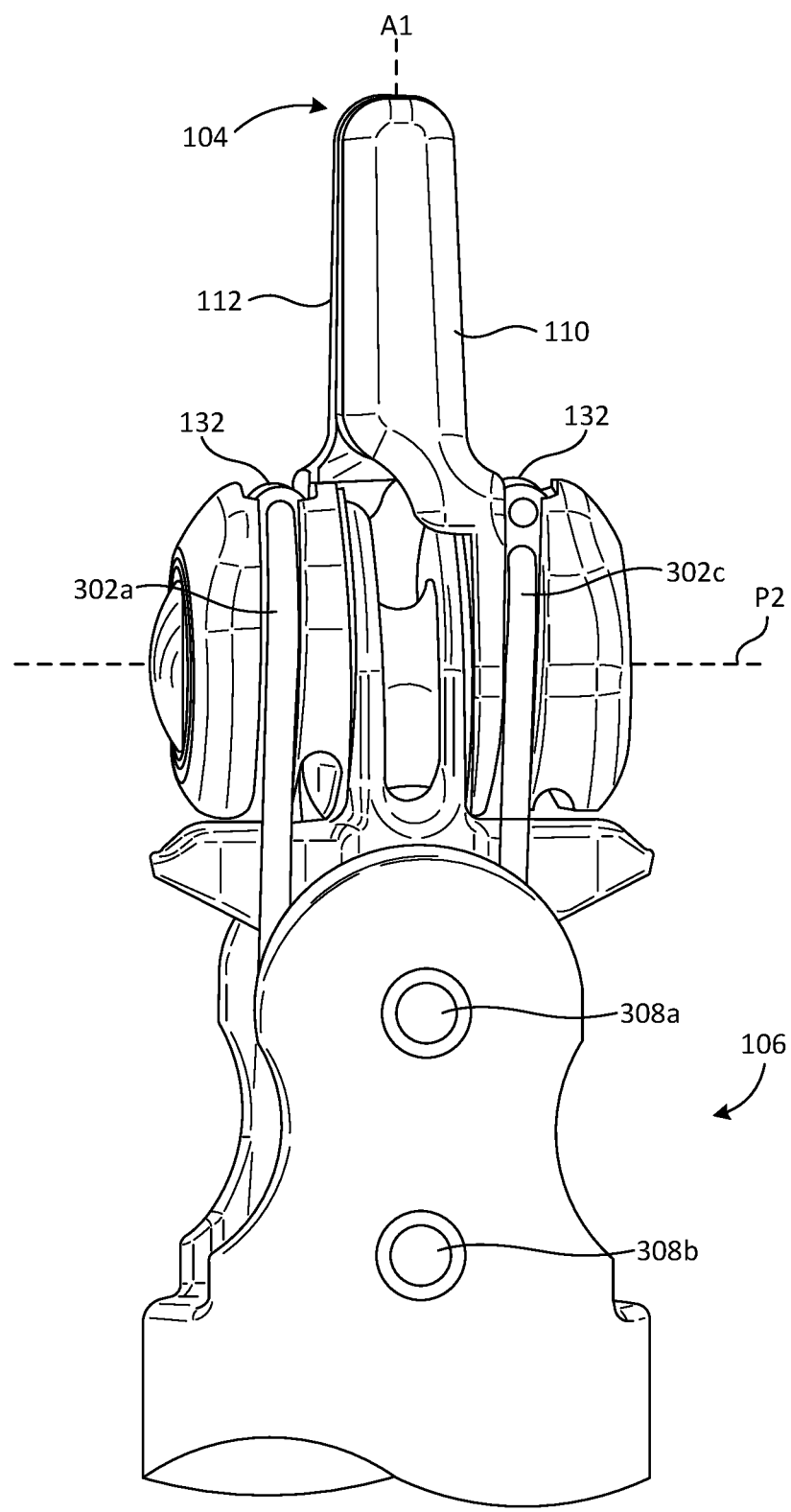

The disposition of cables and similar elongate members within cable-driven surgical tool 100 is illustrated more fully in FIGS. 3-5, which shows an enlarged view of elongate shaft 102, end effector 104, and wrist 106. Although cable-driven surgical tool 100 includes four cables 302a-d as depicted, one pair being operatively coupled to each of jaws 110 and 112, alternative configurations can have differing numbers of cables or similar elongate members. For example, a cable-driven surgical tool having an end effector that does not require internal motion can include two cables or similar elongate members configured to provide articulation upon longitudinal tensioning.

As shown in FIGS. 3-5, cables 302a-d extend longitudinally within lumen 305 of elongate shaft 102 through wrist 106 and operably engage end effector 104, as described hereinafter. The proximal ends of cables 302a-d are similarly operably engaged with components in housing 108 (not shown in FIG. 3). For example, the proximal ends of cables 302a-d may operably engage components in housing 108 that are configured for actuation by one or more drive couplers in the mounting fixture of a robotic surgical system. One or more of cables 302a-d may be selectively translated longitudinally to cause end effector 104 to move (e.g., pivot in one or more locations) relative to elongate shaft 102. Depending on the required motion, one or more of cables 302a-d may translate longitudinally to articulate end effector 104 (e.g., to move jaws 110 and 112 at an angle in a same direction), to open end effector 104 (e.g., to move jaws 110 and 112 away from one another), to close end effector 104 (e.g., to move jaws 110 and 112 toward one other), or any combination thereof.

Although a single lumen 305 is depicted in FIG. 3, multiple lumens can be present in alternative embodiments, such that one or more of cables 302a-d is housed within each of the multiple lumens. In further alternate embodiments, cables 302a-d can extend along the exterior of elongate shaft 102, such as in longitudinal channels formed in an exterior surface of elongate shaft 102.

In the illustrative configuration of FIG. 3, cables 302a-d are present in matched pairs. Depending on how cables 302a-d are translated longitudinally, the range of degrees of freedom depicted in FIG. 2 can be realized.

In some embodiments, first and third cables 302a and 302c define a first cable loop that proximally engages a first location in housing 108 and distally engages a first component of end effector 104 before looping back to engage a second location in housing 108. Similarly, in such embodiments, second and fourth cables 302b and 302d define a second cable loop that proximally engages a third location in housing 108 and distally engages a second component of end effector 104 before looping back to engage a fourth location in housing 108. In other embodiments, cables 302a/302c and 302b/302d are proximally engaged with separate locations in housing 108 and with separate locations at end effector 104. Double barrel element 132 (see FIGS. 4 and 5) may bridge the discontinuity between cables 302a and 302c and between cables 302b and 302d in such embodiments, such that a cable loop is still formed. Suitable means of attachment to double barrel element 132 may include, for example, crimping, welding, adhesive bonding, and the like.

Referring still to FIG. 3, and with further reference to FIGS. 4 and 5, wrist 106 includes multiple pulleys for engaging and redirecting cables 302a-d during their longitudinal translation. Specifically, wrist 106 includes distal plurality of pulleys 316a, 316b, 318a and 318b, and proximal plurality of pulleys 320a, 320b, 322a and 322b. A small gap (best shown in FIG. 4) is defined between corresponding pulleys in the distal and proximal pluralities, which is sized for passage of cables 302a-d therethrough. Pulleys 316a, 316b, 318a and 318b in the distal plurality of pulleys are mounted to distal wrist axle 308a, and pulleys 320a, 320b, 322a and 322b in the proximal plurality of pulleys are mounted to proximal wrist axle 308b. End effector 104 is operably coupled to wrist 106 such that distal wrist axle 308a defines first pivot axis P1 during operation thereof.

Cable-driven surgical tool 100 further includes second pivot axis P2 along end effector axle 303, about which jaws 110 and 112 of end effector 104 are configured to pivot relative to each other between extremes of open and closed positions, and/or about which jaws 110 and 112 are configured to move together during articulation of end effector 104. As illustrated, second pivot axis P2 is substantially perpendicular to longitudinal axis A1. A person having ordinary skill in the art will appreciate that axes A1 and P2 may not be precisely perpendicular to one another but nevertheless be considered to be substantially perpendicular due to any number of factors, such as manufacturing tolerance and precision of measurement devices.

Cable-driven surgical tool 100 has two joints at second pivot axis P2, one joint for each of jaws 110 and 112. Actuation of at least one of cables 302a-d causes movement of jaw 110 and/or jaw 112 at the associated joint(s) along second pivot axis P2. In an exemplary embodiment, jaws 110 and 112 are configured to pivot in tandem at their associated joints. That is, during opening of jaws 110 and 112, each of jaws 110 and 112 rotates at its associated joint, and during closing of jaws 110 and 112, each of jaws 110 and 112 rotates in the opposite direction at its associated joint.

As indicated above, slackening of any of cables 302a-d can compromise the operability of cable-driven surgical tool 100. Even worse, breakage of any of cables 302a-d can render cable-driven surgical tool 100 inoperable. In order to mitigate the risk of cable slackening or breakage during a surgical procedure, it is typical to use cable-driven surgical tool 100 with a generous safety margin of the anticipated operational lifetime of cables 302a-d.

As discussed above, it can be difficult to affect cable replacement in conventional cable-driven surgical tools, such as those depicted illustratively in FIGS. 1 and 3-5. Conventional surgical tools must be essentially disassembled in order to return them to service, if not outright discarded, even though most other components are still within their operational lifetimes. According to various embodiments of the present disclosure, broken, slackened or damaged cables or similar elongate members may be replaced without disassembling the entirety of a cable-driven surgical tool.

Cable replacement may be accomplished through the incorporation of a releasable interconnect interposed between the distal and proximal ends of a cable or similar elongate member. Incorporation of the releasable interconnect allows the distal end of the cable to be replaced without replacing the proximal end. Both cables defining a continuous loop and those being connected by a double barrel element or similar joining element may incorporate releasable interconnects according to the disclosure herein. The term "cable system" is used herein to denote a cable or similar elongate member having a distal cable end and a proximal cable end with a releasable interconnect interposed therebetween. Use of the term "cable system" does not necessarily imply that other types of elongate members cannot be employed in a similar manner. In illustrative embodiments, suitable releasable interconnects may define a male-female joint or coupling, particular examples of which are discussed hereinbelow.

Replacement of the distal end of a cable system may be advantageous. Cable-driven surgical tools are particularly susceptible to cable damage or failure at this location, especially where the cable bends while engaging the pulleys within a wrist or end effector (e.g., due to material fatigue). The limited space in this region, and within cable-driven surgical tools as a whole, limits the cable diameter, which can exacerbate this issue.

Further advantageously, incorporating a releasable interconnect within a cable system can allow a more robust elongate member to constitute the proximal end of the cable system. In conventional cable-driven surgical tools, wherein a cable or similar elongate member of homogeneous character extends between the end effector and the housing, the necessity for a small cable diameter at the wrist and end effector (i.e., the distal cable diameter) similarly limits the proximal cable diameter at the housing. Although not especially spacious, there is commonly more space available in the housing for cable passage than at the distal end of a conventional cable-driven surgical tool. As such, in some embodiments, larger-diameter and/or more robust cables or similar elongate members can extend from the releasable interconnect to the housing in order to convey even more durability to the cable-driven surgical tool. That is, in some embodiments, the distal and proximal cable portions of a cable system may comprise different types or diameters of cables. In other embodiments, however, the material and/or diameter in the distal and proximal cable portions of a cable system can be the same. Accordingly, the disclosure herein can allow rapid wrist repair or replacement to take place for providing more reliable tool function.

Figure 6:
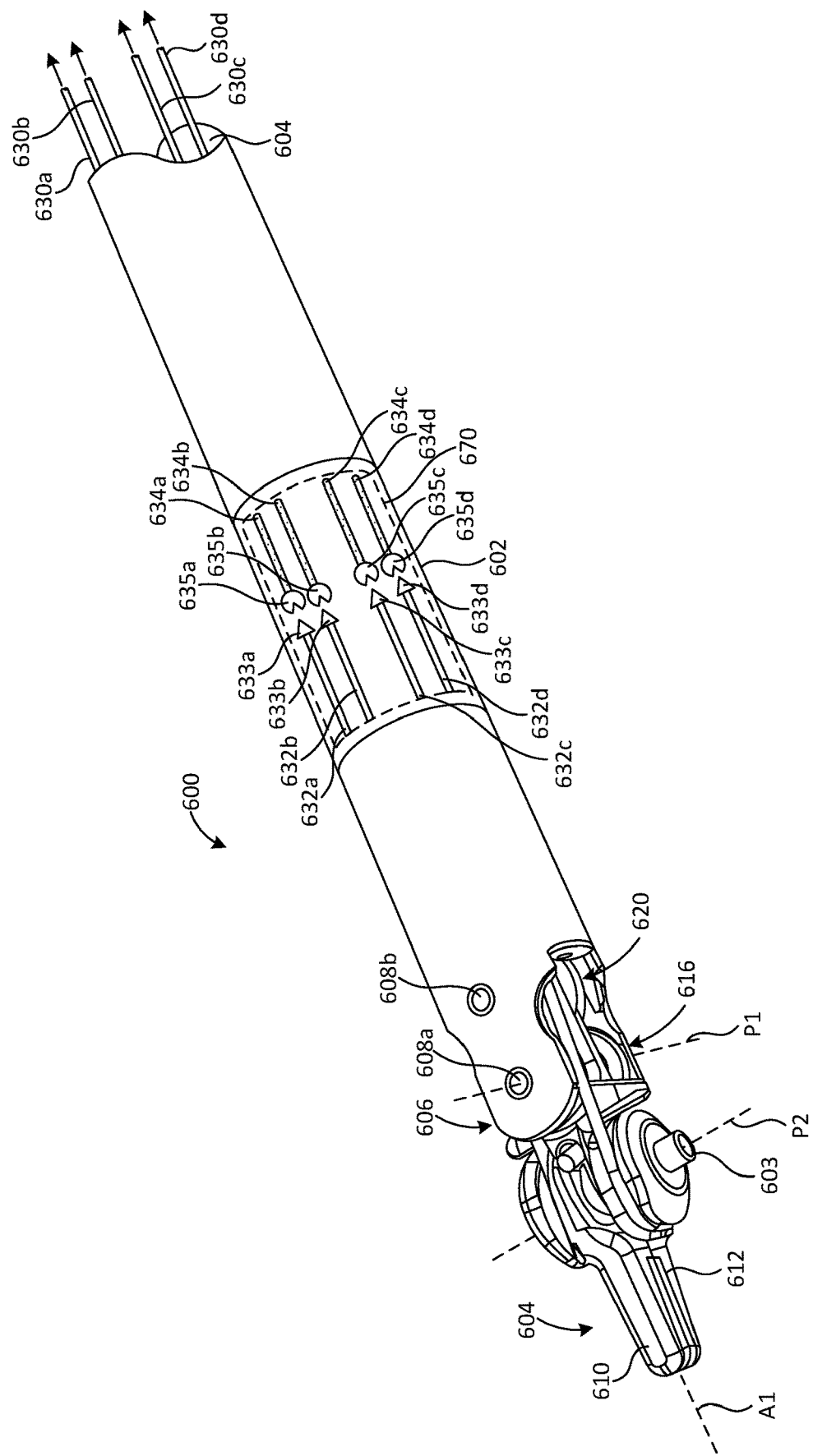
FIG. 6 shows a diagram illustrating a cable-driven surgical tool containing one or more replaceable cable systems.

FIG. 6 is a partial isometric view of illustrative cable-driven surgical tool 600 containing one or more replaceable cable systems. Cable-driven surgical tool 600 is similar in some aspects to cable-driven surgical tool 100 and may be better understood with reference to FIGS. 3-5. As shown in FIG. 6, cable-driven surgical tool 600 includes elongate shaft 602, end effector 604 and wrist 606. Cable systems 630a-d extend through lumen 605 and are operatively engaged distally with end effector 604 and proximally within a housing (not shown in FIG. 6), thereby allowing manipulation of jaws 610 and 612 to take place. As with the embodiments of FIGS. 3-5, the number and configuration of cable systems 630a-d depicted in FIG. 6 are exemplary and non-limiting. Likewise, wrist 606 includes a distal plurality of pulleys 616 and a proximal plurality of pulleys 620. Distal wrist axle 608a and proximal wrist axle 608b correspond to distal and proximal wrist axles 308a and 308b of FIGS. 3-5. Similarly, end effector axle 603, pivot axes P1 and P2, and longitudinal axis A1 all correspond to like elements described previously.

Each cable system 630a-d is divided into corresponding distal cable portion 632a-d and proximal cable portion 634a-d, with a corresponding releasable interconnect adjoining distal cable portions 632a-d and proximal cable portions 634a-d at a junction therebetween. As illustrated, the releasable interconnects may be arranged at a location between wrist 606 and the housing of cable-driven surgical tool 600. Each releasable interconnect includes two connection components configured to mate with one another at the junction in a complementary fashion. As such, first connection components 633a-d of the releasable interconnects are located within lumen 605 at the terminus of each of corresponding distal cable portions 632a-d, and second connection components 635a-d of the releasable interconnects are located within lumen 605 at the terminus of each of corresponding proximal cable portions 634a-d. The manner in which FIG. 6 depicts such mating complementarity is intended to illustrate the concepts of the present disclosure and is not necessarily meant to represent functional interconnectivity. Particular examples of suitable releasable interconnects are discussed in more detail below.

In illustrative embodiments, suitable releasable interconnects that may adjoin distal cable portions 632a-d to proximal cable portions 634a-d in cable-driven surgical tool 600 include, but are not limited to, male-female threading, bayonet connectors, ball connectors, snap connectors (collars), yin-yang connectors (puzzle piece connectors) and the like. These illustrative releasable interconnects are depicted in greater detail in FIGS. 7A, 7B, 8A, 8B, 9A, 9B, 10A, 10B, 11A and 11B in uncoupled and coupled positions. Other types of releasable interconnects that may be suitable for use in the embodiments of the present disclosure include, for example, buckles, clamps, hook and eye connectors, cotters, cotter pins, clevis fasteners, snap fasteners, and the like.

Any of the releasable interconnects disclosed herein may be used in particular configurations of cable-driven surgical tool 600. The same type of releasable interconnect can be present in each of cable systems 630a-d, or at least one of cable systems 630a-d can contain types of releasable interconnects that differ from one another. Furthermore, employing two or more different types of interconnect technologies to form a hybrid releasable interconnect is also possible. For example, a ball connector may further employ a cotter pin to fasten the ball and its receptor together more securely.

Figures 7A, 7B:
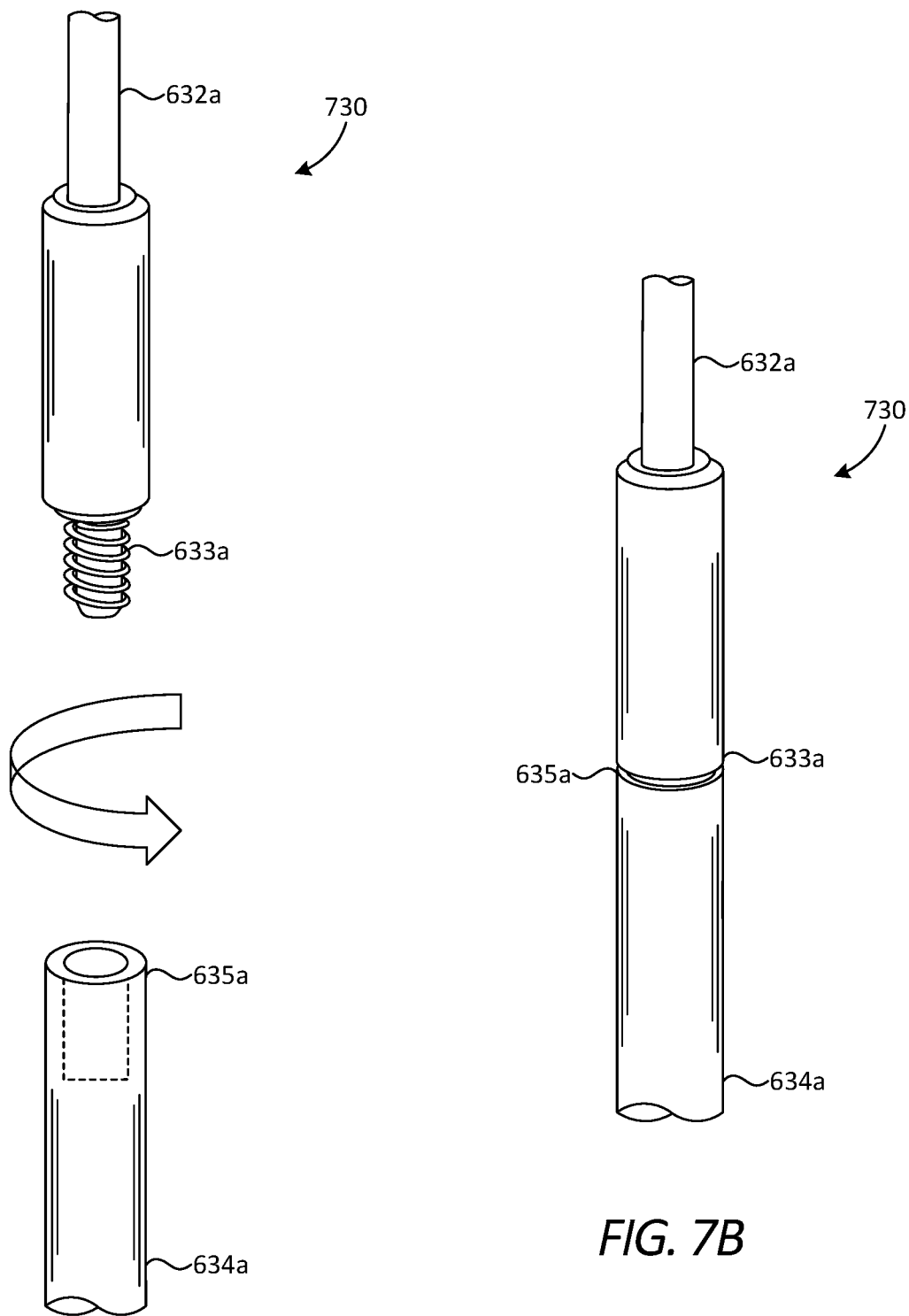
FIGS. 7A, 7B, 8A, 8B, 9A, 9B, 10A, 10B, 11A and 11B show several views of various releasable interconnects in uncoupled and coupled positions.

FIGS. 7A and 7B show an embodiment of cable systems 630a-d that may be used in cable-driven surgical tool 600 of FIG. 6. More particularly, cable system 730 may be representative of any of cable systems 630a-d of FIG. 6 in one or more embodiments. Referring to FIGS. 7A and 7B, first connection component 633a and second connection component 635a are provided as male-female threaded adapters or connectors. The male threading and the female threading may reside on either of distal cable portion 632a or proximal cable portion 634a, and the depicted configuration should not be considered as limiting. Furthermore, the threading pitch, lead, angle, and direction may vary from that depicted, and such considerations will be familiar to one having ordinary skill in the art.

Figures 8A, 8B:
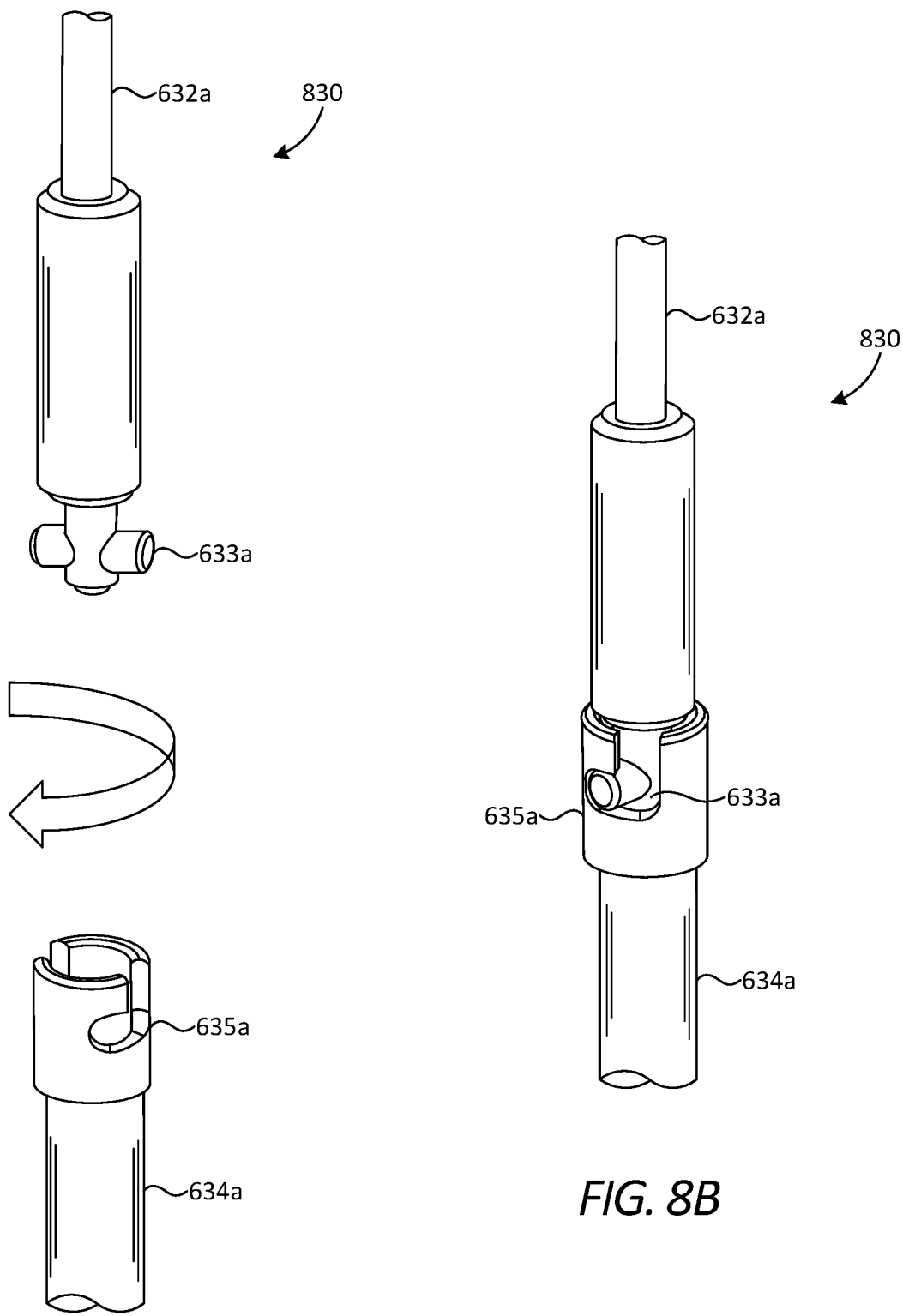

FIGS. 8A and 8B show another embodiment of cable systems 630a-d that may be used in cable-driven surgical tool 600 of FIG. 6. More particularly, cable system 830 may be representative of any of cable systems 630a-d of FIG. 6 in one or more embodiments. Referring to FIGS. 8A and 8B, first connection component 633a and second connection component 635a are provided as corresponding bayonet connectors. As with male-female threading, the male portion (i.e., first connection component 633a) and the female portion (i.e., second connection component 635a) of the bayonet connector may reside on either of distal cable portion 632a or proximal cable portion 634a, and the depicted configuration should not be considered as limiting. Furthermore, the design of the bayonet connector may vary from that depicted, and one having ordinary skill in the art will be able to choose a suitable bayonet connector for a given application.

Figures 9A, 9B:
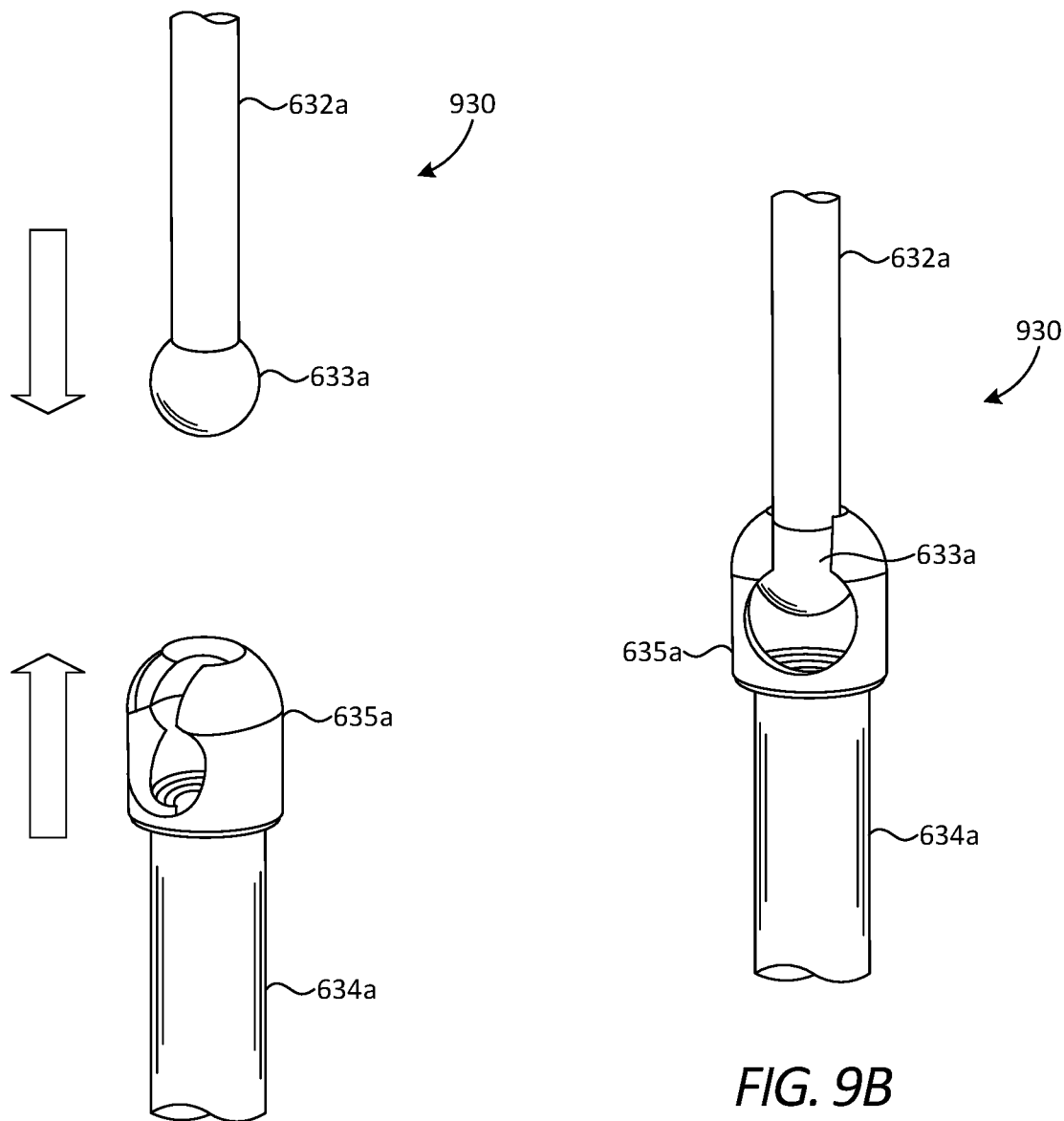

FIGS. 9A and 9B show another embodiment of cable systems 630a-d that may be used in cable-driven surgical tool 600 of FIG. 6. More particularly, cable system 930 may be representative of any of cable systems 630a-d of FIG. 6 in one or more embodiments. Referring to FIGS. 9A and 9B, first connection component 633a and second connection component 635a are provided as corresponding parts of a ball connector. Cable tensioning maintains the ball (i.e., first connection component 633a) within its receptor (i.e., second connection component 635a). As with other types of releasable interconnects, the ball and the receptor of a ball joint may reside on either of distal cable portion 632a or proximal cable portion 634a, and the depicted configuration and design should not be considered as limiting.

Figures 10A, 10B:
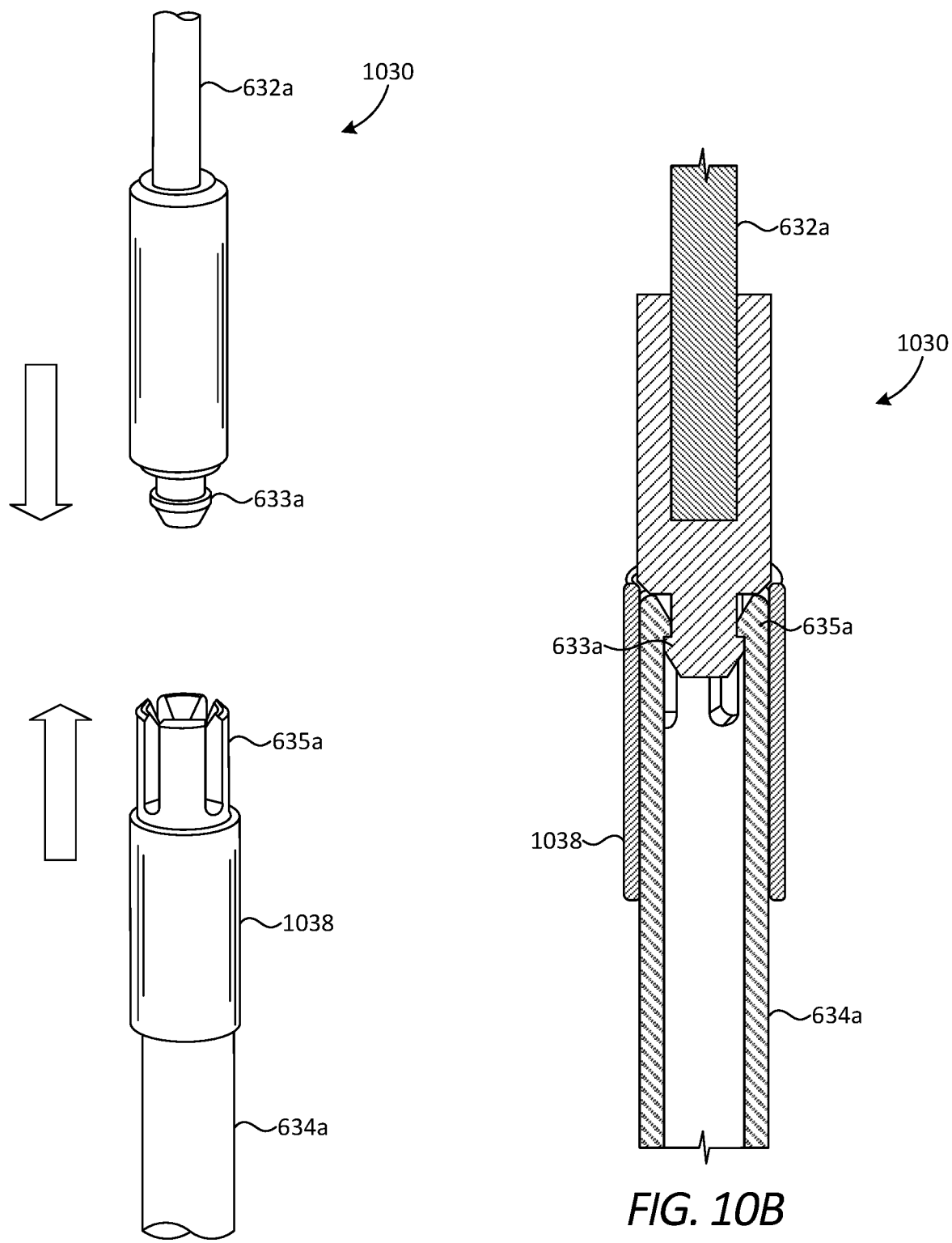

FIGS. 10A and 10B show another embodiment of cable systems 630a-d that may be used in cable-driven surgical tool 600. More particularly, cable system 1030 may be representative of any of cable systems 630a-d of FIG. 6 in one or more embodiments. Referring to FIGS. 10A and 10B, first connection component 633a and second connection component 635a are provided as corresponding parts of a snap connector (snap collar). In the depicted embodiment, a flanged stud (i.e., first connection component 633a) mates with a corresponding receptor (i.e., second connection component 635a), and collar 1038 is then moved (slid) over the mated joint to hold the components in place, as shown in cutaway in FIG. 10B. Collar 1038 constricts the receptor to hold the inserted flanged stud in place. Alternately, heat shrink tubing or manual crimping, for example, may be used interchangeably to hold the flanged study within its corresponding receptor. In some embodiments, however, collar 1038 may be omitted if the flanged stud and receptor can be held in place without it. As with other types of releasable interconnects, the flanged stud and receptor may reside on either of distal cable portion 632a or proximal cable portion 634a, and the depicted configuration and design should not be considered as limiting.

Figures 11A, 11B:
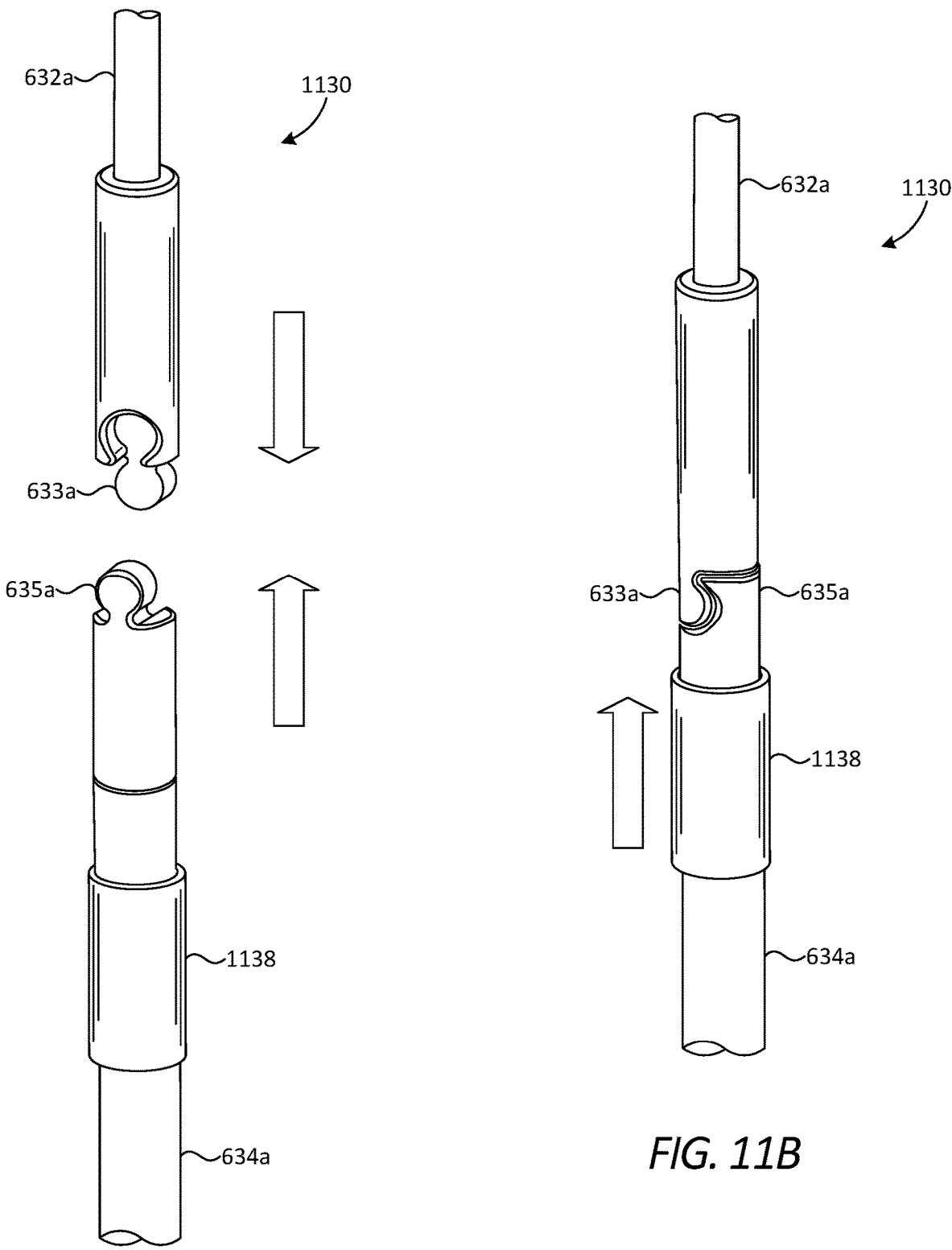

FIGS. 11A and 11B show another embodiment of cable systems 630a-d that may be used in cable-driven surgical tool 600. More particularly, cable system 1130 may be representative of any of cable systems 630a-d of FIG. 6 in one or more embodiments. Referring to FIGS. 11A and 11B, a yin-yang connector (puzzle-piece connector) defines first complementary component 633a and second complementary component 635a. In this case, once the puzzle-like pieces are mated together to define a joint, sleeve 1138 is slid over the mated joint to hold the components in place. In some embodiments, sleeve 1138 may be heat shrink tubing that can be heated and constricted to hold the components in place. Other suitable configurations for sleeve 1138 may include, for example, interference fit tubing, crimped tubing, mechanically fastened tubing and the like. FIG. 11B shows the disposition of sleeve 1138 prior to sliding over the mated joint. Still further alternately, sleeve 1138 may be omitted if the mated joint can be held in place without it. As with other types of releasable interconnects, the depicted configuration and design should not be considered as limiting.

Referring again to FIG. 6, the relative axial location of the releasable interconnects in cable systems 630a-d with respect to wrist 606 are not particularly limited. However, in some embodiments, it may be more advantageous for the releasable interconnects to be located closer to wrist 606 as opposed to housing 108 (FIG. 1), as the former is where cable wear more commonly occurs. That is, in such embodiments, the releasable interconnects may be axially offset toward the distal end of elongate shaft 602. Releasable interconnects that are located closer to housing 108, however, are also possible without departing from the scope of the disclosure. Furthermore, in some embodiments, all of the releasable interconnects are located at substantially the same axial location within lumen 605, although they may be located at different axial locations in other embodiments.

Regardless of the axial position of the releasable interconnects within lumen 605, a suitable route for accessing the releasable interconnects from the exterior of elongate shaft 602 may be provided. Sealing in proximity to the access location to lumen 605 can be provided, if needed, to aid in maintaining insufflation, for example, according to some embodiments. In some embodiments, elongate shaft 602 may have a distal section and a proximal section that are releasably coupled to one another so as to provide access to the releasable interconnects when opened. Suitable mechanisms by which the distal and proximal sections may be releasably coupled together include, for example, a threaded engagement, one or more mechanical fasteners, a compression fit, spring-loaded clips, bayonet-style connectors, oval connectors, snap connectors, the like, and any combination thereof. In other embodiments, elongate shaft 602 may have window 670 defined therein in order to provide access to the releasable interconnects within lumen 605. In some embodiments, window 670 may by obscured during use with a removable cover, such as a sleeve, a panel, a hatch, or the like. In other embodiments, window 670 may be left open, thereby allowing ongoing access to lumen 605 to be realized, provided that insufflation loss is not an issue.

The incorporation of a releasable interconnect within a cable system can increase the cable diameter considerably over that of the cable alone at a junction between the distal and proximal cable portions. The increased diameter in a cable system can be problematic in some instances. Specifically, the limited clearance between pulleys at the wrist of conventional cable-driven surgical tools, particularly the clearance between the distal and proximal plurality of pulleys, can make cable threading problematic when a releasable interconnect is present.

As such, the inventor also discovered various approaches whereby the clearance in a wrist may be increased temporarily, if needed, to facilitate threading of a replacement cable. Specifically, the inventor discovered ready ways to alter or disassemble a wrist partially to facilitate cable threading. The partial disassembly approaches discovered by the inventor are considerably more facile than the complete disassembly required for repair of conventional cable-driven surgical tools. Furthermore, the partial disassembly approaches of the present disclosure can also be practiced independently of embodiments incorporating a releasable interconnect as described herein.

The releasable interconnects interposed in cable systems 630*a-d* can be problematic when threading distal cable portions 632*a-d* through the limited space in wrist 606. To address this issue, the inventor also developed several approaches for temporarily increasing the clearance in wrist 606 to facilitate cable threading between the distal and proximal pluralities of pulleys. Specifically, in various embodiments of the present disclosure, wrist 606 can be partially disassembled readily in order to promote cable threading. Although the partial disassembly approaches disclosed herein may facilitate threading of cable systems containing a releasable interconnect, the same or similar approaches may also be practiced independently, such as when threading conventional cables and like elongate members. Furthermore, in some or other embodiments, the same or similar approaches may be practiced independently in conjunction with exchanging one type of end effector for another after the completion of a surgical procedure.

FIGS. 12A-12C show isometric and cross-sectional views of one approach for generating clearance in a wrist of a cable-driven surgical tool. As shown in FIG. 12A, end effector 1204 of surgical tool 1200 is operably connected to wrist 1206 with wrist axle 1250, which defines pivot axis P1. As best shown in FIG. 12C, a distal plurality of pulleys 1216 and a proximal plurality of pulleys 1220 are present for guiding cable systems or similar elongate members through wrist 1206. Distal plurality of pulleys 1216 are mounted to wrist axle 1250, which simultaneously connects end effector 1204 to wrist 1206 via distal clevis 1240. Wrist axle 1260 operably connects proximal plurality of pulleys 1220 to proximal clevis 1270.

As illustrated, wrist axle 1250 also extends through a pair of pivot discs 1252 (only one shown in FIGS. 12A and 12B) movably coupled to proximal clevis 1270. Each pivot disc 1252 has a centerline that is radially offset from the pivot axis P1. Thus, pivot axis P1 does not pass through the centerline of pivot discs 1252 (i.e., is eccentric), in contrast to the tool configurations depicted in FIGS. 2-6.

Pivot discs 1252 are configured for rotation relative to proximal clevis 1270 and may be rotated incrementally to alter the location of pivot axis P1. In some embodiments, pivot discs 1252 may be rotated with one's fingers, or they may be configured to be rotated using a specialized tool, such as a screwdriver, Allen wrench, or similar tool. Pivot discs 1252 may rotate freely or semi-freely in some embodiments. That is, in such embodiments, pivot discs 1252 are not necessarily constrained to just two rotational positions. In other embodiments, pivot discs 1252 may be configured to rotate between a first locked position and a second locked position upon affecting rotational motion. In exemplary embodiments, the first locked position and the second locked position are disposed substantially 180° apart from one another. In other embodiments, the first locked position and the second locked position are between 90° and 180° apart from one another, or between 110° and 180° apart from one another, or between 130° and 180° apart from one another, or between 150° and 180° apart from one another.

Since pivot axis P1 is eccentric to the centerline of pivot discs 1252, rotation of pivot discs 1252 correspondingly repositions pivot axis P1. For example, in the case of rotating pivot discs 1252 by 180°, a maximum displacement of pivot axis P1 occurs in rotating from the first position to the second position. Displacement of pivot axis P1 also causes a corresponding displacement in distal plurality of pulleys 1216 and distal clevis 1240, through which wrist axle 1250 passes.

FIG. 12A shows pivot discs 1252 in a first position, such that pivot axis P1 is situated with distal plurality of pulleys 1216 and proximal plurality of pulleys 1220 in near engagement with one another. FIGS. 12B and 12C show pivot discs 1252 in a second position. More specifically, rotation of pivot disc 1252 by 180° moves pivot axis P1 distally, thereby displacing distal clevis 1240 and increasing a separation distance between distal plurality of pulleys 1216 and proximal plurality of pulleys 1220. Although FIGS. 12A and 12B have illustrated a near-180° rotation of pivot disc 1252, it is to be recognized that non-180° rotational angles may also affect sufficient pulley separation and may be employed in the embodiments of the present disclosure.

Once wrist 1206 has been threaded to load the distal cable portion of a replacement cable, pivot discs 1252 may be rotated in the opposite direction to return distal plurality of pulleys 1216 to the first (original) position. At this point, cable-driven surgical tool 1200 may return to service or undergo recalibration, if neeeded.

Figure 13C:
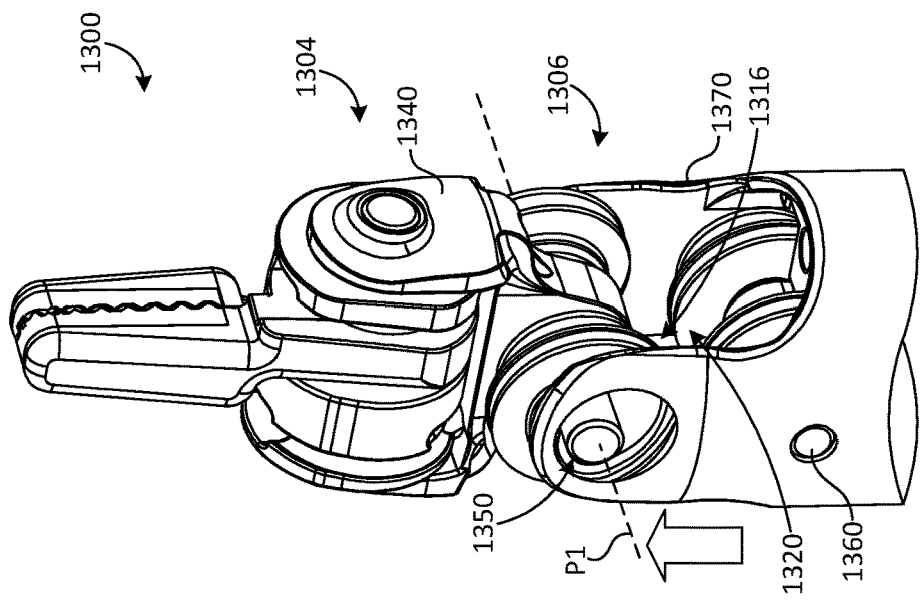
FIGS. 13A-13C show diagrams illustrating a second approach for generating clearance in a wrist of a cable-driven surgical tool.
Figure 13B:
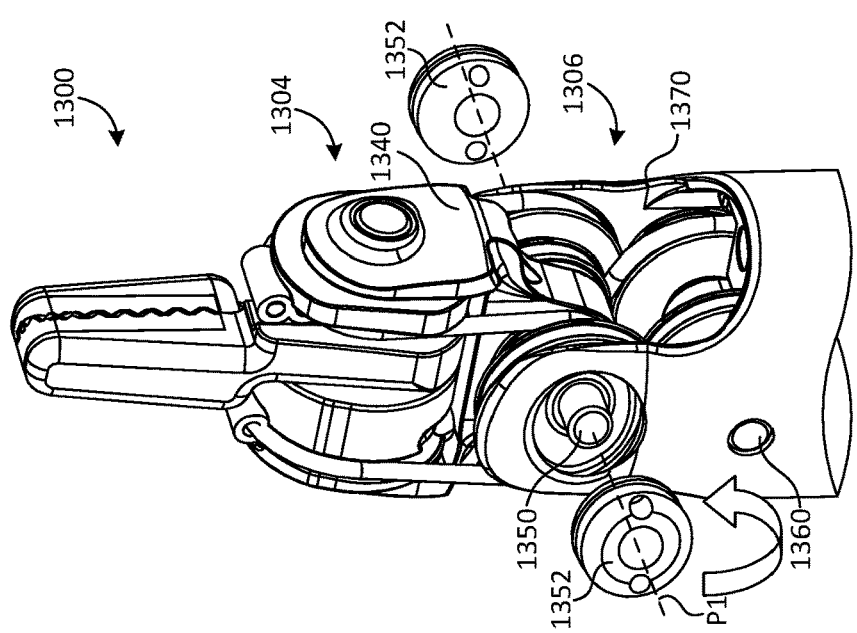
Figure 13A:
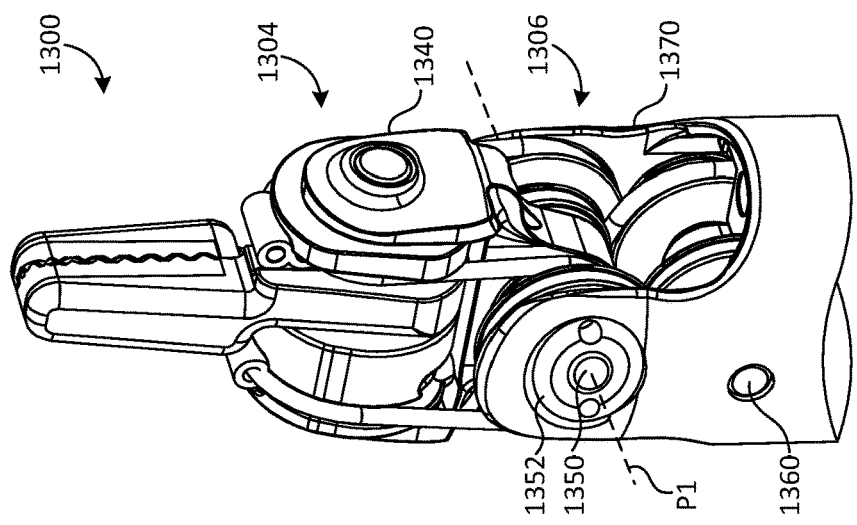

FIGS. 13A-13C show isometric views of a second approach for generating clearance in a wrist of a cable-driven surgical tool. In contrast to the approach depicted in FIGS. 12A-12C, in which all components remain operably connected together but in different positions, the approach depicted in FIGS. 13A-13C provides for removal of the pivot discs in the course of increasing the separation distance between the distal plurality of pulleys and the proximal plurality of pulleys.

Referring to FIG. 13A, end effector 1305 is operably connected to wrist 1306 with wrist axle 1350 in cable-driven surgical tool 1300. Wrist axle 1350 defines pivot axis P1. A distal plurality of pulleys 1316 and a proximal plurality of pulleys 1320 are present for guiding cable systems or similar elongate members through wrist 1306. Wrist axle 1350 passes through distal plurality of pulleys 1316 and proximal clevis 1370 in operably connecting end effector 1305 to wrist 1306. Wrist axle 1360 operably connects proximal plurality of pulleys 1320 to proximal clevis 1370. Wrist axle 1350 extends through pivot discs 1352, which are removably coupled to proximal clevis 1370. Although wrist axle 1350 is depicted as passing through the center of pivot discs 1352, the disclosure is not limited in this aspect.

In illustrative embodiments, pivot discs 1352 may be removably coupled to proximal clevis 1370 via threading. In such embodiments, pivot discs 1352 may be rotated clockwise or counterclockwise to affect their removal from proximal clevis 1370. In other embodiments, pivot discs 1352 may be removably coupled to proximal clevis 1370 in a non-threaded manner, such as via a compression fitting, latching mechanism, or the like. In either case, removal of pivot discs 1352 from proximal clevis 1370 may be affected manually, with a tool or combinations thereof. In some instances, pivot discs 1352 may be removed from proximal clevis 1370 without being rotated.

Upon removal of pivot discs 1352 from wrist 1306, distal plurality of pulleys 1316 and end effector 1305 remain coupled via wrist axle 1350 but are then free to move with an increased range of motion, either side-to-side or upward with respect to proximal plurality of pulleys 1320. For example, as depicted in FIG. 13C, end effector 1305, distal plurality of pulleys 1316 and wrist axle 1350 may be moved upwardly to increase the separation between distal plurality of pulleys 1316 and proximal plurality of pulleys 1320.

Once wrist 1306 has been threaded to load the distal cable portion of a replacement cable, end effector 1305, distal plurality of pulleys and wrist axle 1350 may be lowered into their original position, such that the replacement cable properly engages proximal plurality of pulleys 1320. Pivot discs 1352 may then be reinserted into proximal clevis 1370 to ready cable-driven surgical tool 1300 for service or recalibration.

Accordingly, in addition to the cable-driven surgical tools described hereinabove, the present disclosure also provides various methods for replacing a cable within a cable-driven surgical tool, such as those disclosed herein. Cable replacement can occur at periodic intervals, in response to cable slackening, in response to cable breakage, or any combination thereof. Any or all of the cables within a surgical tool may be replaced at the same time or at different times according to the methods described herein.

More specifically, in various embodiments, cable replacement methods of the present disclosure may comprise: accessing a plurality of cable systems of a cable-driven surgical tool, each cable system extending with a lumen defined in an elongate shaft and operably engaging an end effector operably coupled to a distal end of the elongate shaft, where each cable system comprises a distal cable portion and a proximal cable portion adjoined by a releasable interconnect and each releasable interconnect comprises a first connection component located at a terminus of the distal cable portion and a second connection component located at a terminus of the proximal cable portion; disconnecting the first connection component from the second connection component of at least one of the plurality of cable systems; removing a disconnected distal cable portion from the cable-driven surgical tool; introducing a replacement distal cable portion also having a first connection component into the cable-driven surgical tool; and mating the first connection component of the replacement distal cable portion to an unmated second complementary component in the lumen. Any of the various cable-driven surgical tools and releasable interconnects discussed herein may be employed in the cable replacement methods of the present disclosure.

In further embodiments, methods of the present disclosure may comprise accessing the releasable interconnect by disconnecting a distal section of the elongate shaft of the cable-driven surgical tool from a proximal cable portion of the elongate shaft of the surgical tool. In some or other further embodiments, methods of the present disclosure may comprise accessing the releasable interconnect through a window defined in the elongate shaft of the cable-driven surgical tool.

Embodiments disclosed herein include:

A. Cable-driven surgical tools: The cable-driven surgical tools comprise: an elongate shaft defining a lumen that extends between a proximal end and a distal end of the elongate shaft; an end effector operably coupled to the distal end of the elongate shaft; and a plurality of cable systems extending within the lumen and operably engaging the end effector, each cable system comprising a distal cable portion and a proximal cable portion adjoined by a releasable interconnect.

B. Cable-driven surgical tools for a robotic manipulator. The cable-driven surgical tools comprise: an elongate shaft defining a lumen that extends between a proximal end and a distal end of the elongate shaft; an end effector operably coupled to the distal end of the elongate shaft; a plurality of cable systems extending within the lumen and operably engaging the end effector, each cable system comprising a distal cable portion and a proximal cable portion adjoined by a releasable interconnect; wherein the releasable interconnect is selected from the group consisting of male-female threading, a bayonet connector, a ball connector, a snap connector, and a yin-yang connector; and a housing operably coupled to the proximal end of the elongate shaft; wherein the housing is configured for releasable coupling with a robotic manipulator.

C. Methods for using a cable-driven surgical tool. The methods comprise: accessing a plurality of cable systems of a cable-driven surgical tool, each cable system extending within a lumen defined in an elongate shaft and operably engaging an end effector operably coupled to a distal end of the elongate shaft; wherein each cable system comprises a distal cable portion and a proximal cable portion adjoined by a releasable interconnect, each releasable interconnect comprising a first connection component located at a terminus of the distal cable portion and a second connection component located at a terminus of the proximal cable portion; disconnecting the first connection component from the second connection component of at least one of the plurality of cable systems; after disconnecting, removing a disconnected distal cable portion from the cable-driven surgical tool; introducing a replacement distal cable portion into the cable-driven surgical tool, the replacement distal cable portion also having a first connection component; and mating the first connection component of the replacement distal cable portion to an unmated second connection component in the lumen.

Each of embodiments A, B, and C may have one or more of the following additional elements in any combination Element 1: wherein each releasable interconnect comprises a first connection component located at a terminus of the distal cable portion and a second connection component located at a terminus of the proximal cable portion, the first connection component and the second connection component being configured to mate with one another at a junction.

Element 2: wherein the releasable interconnect is selected from the group consisting of male-female threading, a bayonet connector, a ball connector, a snap connector, and a yin-yang connector.

Element 3: wherein each releasable interconnect is axially offset toward the distal end of the elongate shaft.

Element 4: wherein the cable-driven surgical tool further comprises a window defined in the elongate shaft and providing access to each releasable interconnect within the lumen.

Element 5: wherein the elongate shaft comprises a distal section releasably coupled to a proximal section.

Element 6: wherein the distal cable portion and the proximal cable portion comprise different types or diameters of cables.

Element 7: wherein the cable-driven surgical tool further comprises a housing operably coupled to the proximal end of the elongate shaft; wherein the housing is configured for releasable coupling with a robotic manipulator.

Element 8: wherein the plurality of cable systems are configured to articulate the end effector.

Element 9: wherein the cable-driven surgical tool further comprises a wrist that movably couples the end effector to the distal end of the elongate shaft.

Element 10: wherein the end effector is movably coupled to the distal end of the elongate shaft via a pivot joint in the wrist.

Element 11: wherein each releasable interconnect is selected from the group consisting of male-female threading, a bayonet connector, a ball connector, a snap connector, and a yin-yang connector.

Element 12: wherein the replacement distal cable portion is threaded between a plurality of pulleys located in a wrist movably coupling the end effector to the distal end of the elongate shaft.

Element 13: wherein accessing the plurality of cable systems comprises disconnecting a distal section of the elongate shaft from a proximal section of the elongate shaft.

Element 14: wherein the plurality of cable systems are accessed through a window defined in the elongate shaft.

By way of non-limiting example, exemplary combinations applicable to A include: 1 and 2; 1 and 3; 2 and 3; 1 and 4; 2 and 4; 3 and 4; 1 and 5; 2 and 5; 3 and 5; 2 and 6; 2 and 7; 2 and 8; 7 and 8; 7 and 9; and 2 and 9.

By way of non-limiting example, exemplary combinations applicable to B include: 1 and 3; 1 and 4; 1 and 5; 3 and 5; 4 and 5; 3 and 4; 3 and 5; 3 and 6; 4 and 6; 5 and 6; 8 and 9; 8 and 10; 4 and 9; and 4 and 10.

By way of non-limiting example, exemplary combinations applicable to C include: 11 and 12; 11 and 13; 11 and 14; 12 and 13; and 12 and 14.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is following:

1. A method of replacing cables in a cable-driven surgical tool, comprising:
accessing a cable system of the cable-driven surgical tool, the cable-driven surgical tool including:
an elongate shaft defining a lumen that extends between proximal and distal ends of the elongate shaft; and
an end effector operatively coupled to the distal end of the elongate shaft, wherein the cable system comprises distal and proximal cable portions extending within the lumen and adjoined by a releasable interconnect, and wherein the distal cable portion is operatively coupled to the end effector;
disconnecting the distal and proximal cable portions at the releasable interconnect, wherein the distal cable portion exhibits a first diameter and the proximal cable portion exhibits a second diameter greater than the distal cable portion;
removing the distal cable portion; and
mating a replacement distal cable portion to the proximal cable portion.

2. The method of claim 1, wherein the releasable interconnect comprises a first connection component located at a terminus of the distal cable portion and a second connection component located at a terminus of the proximal cable portion, and wherein removing the distal cable portion comprises detaching the first connection component from the second connection component.

3. The method of claim 2, wherein the releasable interconnect is selected from the group consisting of male-female threading, a bayonet connector, a ball connector, a snap connector, and a yin-yang connector.

4. The method of claim 1, wherein accessing the cable system comprises disconnecting a distal section of the elongate shaft from a proximal section of the elongate shaft.

5. The method of claim 1, wherein accessing the cable system comprises accessing the cable system via a window defined in the elongate shaft.

6. The method of claim 1, further comprising articulating the end effector with the cable system.

7. The method of claim 1, wherein the distal cable portion and the proximal cable portion comprise different materials.

8. The method of claim 1, wherein the cable-driven surgical tool further includes a wrist that interposes the end effector and the distal end of the elongate shaft, wherein the wrist includes:
a proximal clevis coupled to the distal end of the elongate shaft;
a pair of pivot discs rotationally coupled to the proximal clevis and providing a centerline extending through a center of each pivot disc;
a distal plurality of pulleys mounted to the proximal clevis at a distal wrist axle extending through the pair of pivot discs, the distal wrist axle having a pivot axis radially offset from the centerline of the pair of pivot discs; and
a proximal plurality of pulleys mounted to the proximal clevis at a proximal wrist axle and offset from the distal plurality of pulleys by a gap,
the method further comprising rotating the pair of pivot discs and thereby moving the distal plurality of pulleys to adjust a size of the gap between the proximal and distal pluralities of pulleys.

9. The method of claim 8, further comprising moving the pair of pivot discs between a first locked position and a second locked position angularly offset from the first locked position.

10. The method of claim 8, further comprising rotatably coupling the end effector to the distal wrist axle.

11. The method of claim 1, wherein the releasable interconnect is located closer to the distal end of the elongate shaft rather than the proximal end of the elongate shaft.

12. A method of replacing cables in a robotic cable-driven surgical tool, comprising:
detaching the cable-driven surgical tool from an arm of a robotic manipulator, the cable-driven surgical tool including a housing removably attachable to the arm, an elongate shaft extending from the housing, and an end effector operatively coupled to a distal end of the shaft;
accessing a cable system of the cable-driven surgical tool, the cable system comprising distal and proximal cable portions extending within the shaft and adjoined by a releasable interconnect, wherein the distal cable portion is operatively coupled to the end effector;
disconnecting the distal and proximal cable portions at the releasable interconnect, wherein the distal cable portion exhibits a first diameter and the proximal cable portion exhibits a second diameter greater than the distal cable portion;
removing the distal cable portion; and
mating a replacement distal cable portion to the proximal cable portion.

13. The method of claim 12, wherein the releasable interconnect comprises a first connection component located at a terminus of the distal cable portion and a second connection component located at a terminus of the proximal cable portion, and wherein removing the distal cable portion comprises detaching the first connection component from the second connection component.

14. The method of claim 13, wherein the releasable interconnect is selected from the group consisting of male-female threading, a bayonet connector, a ball connector, a snap connector, and a yin-yang connector.

15. The method of claim 12, wherein accessing the cable system comprises disconnecting a distal section of the elongate shaft from a proximal section of the elongate shaft.

16. The method of claim 12, wherein accessing the cable system comprises accessing the cable system via a window defined in the elongate shaft.

17. The method of claim 12, wherein detaching the cable-driven surgical tool from the arm of the robotic manipulator is preceded by articulating the end effector with the cable system.

18. The method of claim 12, wherein the cable-driven surgical tool further includes a wrist that interposes the end effector and the distal end of the elongate shaft, wherein the wrist includes:
a proximal clevis coupled to the distal end of the elongate shaft;
a pair of pivot discs rotationally coupled to the proximal clevis and providing a centerline extending through a center of each pivot disc;
a distal plurality of pulleys mounted to the proximal clevis at a distal wrist axle extending through the pair of pivot discs, the distal wrist axle having a pivot axis radially offset from the centerline of the pair of pivot discs; and
a proximal plurality of pulleys mounted to the proximal clevis at a proximal wrist axle and offset from the distal plurality of pulleys by a gap, the method further comprising rotating the pair of pivot discs and thereby moving the distal plurality of pulleys to adjust a size of the gap between the proximal and distal pluralities of pulleys.

19. The method of claim 18, further comprising moving the pair of pivot discs between a first locked position and a second locked position angularly offset from the first locked position.

20. The method of claim 18, further comprising rotatably coupling the end effector to the distal wrist axle.

* * * * *